(12) United States Patent
Spang, Jr. et al.

(10) Patent No.: US 8,167,259 B2
(45) Date of Patent: May 1, 2012

(54) RAPID ATTACH AND RELEASE CLAMPS

(75) Inventors: Ronald H. Spang, Jr., Kenosha, WI (US); John Marchese, Grayslake, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 225 days.

(21) Appl. No.: 12/418,964

(22) Filed: Apr. 6, 2009

(65) Prior Publication Data

US 2010/0252702 A1    Oct. 7, 2010

(51) Int. Cl.
  *A47B 96/06* (2006.01)
(52) U.S. Cl. ............. 248/230.4; 248/218.4; 248/229.14
(58) Field of Classification Search ............ 248/229.14, 248/229.24, 228.5, 230.5, 231.61, 229.13, 248/229.23, 228.4, 230.4, 231.51, 316.1, 248/316.5, 218.4, 230.1, 219.4
See application file for complete search history.

(56) References Cited

U.S. PATENT DOCUMENTS

| | | | |
|---|---|---|---|
| 904,485 A | 11/1908 | Johnson | |
| 1,359,775 A | 11/1920 | White | |
| 1,589,307 A | 6/1926 | Svebilius | |
| 2,382,811 A * | 8/1945 | Papkin | 241/285.1 |
| 2,452,849 A | 11/1948 | Gross | |
| 2,553,802 A | 5/1951 | Woods | |
| 2,584,955 A | 2/1952 | Williams | |
| 2,671,482 A | 3/1954 | Gordon | |
| 2,832,560 A | 4/1958 | Grigsby | |
| 2,882,774 A | 4/1959 | Guttfeld | |
| 3,265,032 A | 8/1966 | Hume | |
| 3,570,836 A | 3/1971 | Pettavel | |
| 3,706,437 A | 12/1972 | Eberhardt | |
| 3,765,061 A | 10/1973 | Nash | |
| 3,878,757 A | 4/1975 | Puklus, Jr. | |
| 4,048,878 A | 9/1977 | Nystrom | |
| 4,134,499 A | 1/1979 | Joswig | |
| 4,190,224 A * | 2/1980 | LeBlanc et al. | 248/227.3 |
| 4,217,847 A | 8/1980 | McCloud | |
| 4,445,657 A * | 5/1984 | Breckenridge | 248/73 |
| 4,674,722 A * | 6/1987 | Danby et al. | 248/231.31 |
| 4,729,535 A | 3/1988 | Frazier et al. | |

(Continued)

FOREIGN PATENT DOCUMENTS

GB    731988    6/1955

(Continued)

OTHER PUBLICATIONS

International Search Report for Application No. PCT/EP2010/027610 dated Aug. 5, 2010, 4 pages.

(Continued)

*Primary Examiner* — Nkeisha Smith
(74) *Attorney, Agent, or Firm* — K&L Gates LLP (57) ABSTRACT

Rapid attach and release clamps for attaching to supports include a threaded rod, an arm pivotally attached to the threaded rod, and a knob having an exterior surface and an interior surface. The knob defines a passageway sized to fit the threaded rod. A lock comprises at least one thread and is rotatably attached to the interior surface of the knob. The lock is constructed and arranged to move between a closed position with the thread entering the passageway and engaging the threaded rod and an open position with the thread not entering the passageway. A lever is moveably attached to the clamp and constructed and arranged to rotate the lock about a pivot point.

13 Claims, 7 Drawing Sheets

U.S. PATENT DOCUMENTS

| | | | |
|---|---|---|---|
| 4,832,299 A | 5/1989 | Gorton et al. | |
| 4,844,397 A | 7/1989 | Skakoon et al. | |
| 4,997,154 A | 3/1991 | Little | |
| 5,149,036 A | 9/1992 | Sheehan | |
| 5,169,106 A * | 12/1992 | Rasmussen | 248/230.3 |
| 5,174,533 A | 12/1992 | Pryor et al. | |
| 5,222,420 A | 6/1993 | Sorenson et al. | |
| 5,322,253 A | 6/1994 | Stevens | |
| 5,332,184 A | 7/1994 | Davis | |
| 5,561,890 A | 10/1996 | Rich | |
| 5,584,457 A | 12/1996 | Fawcett | |
| D382,471 S | 8/1997 | Neff | |
| 5,701,991 A * | 12/1997 | Helmetsie | 198/836.1 |
| 5,779,207 A * | 7/1998 | Danby | 248/230.4 |
| 5,785,480 A | 7/1998 | Difeo | |
| 5,829,723 A | 11/1998 | Brunner et al. | |
| 5,836,559 A * | 11/1998 | Ronci | 248/230.3 |
| 5,868,538 A | 2/1999 | Rathbun | |
| 5,898,974 A | 5/1999 | Boyer | |
| 5,964,440 A | 10/1999 | An et al. | |
| 6,017,008 A | 1/2000 | Farley | |
| 6,024,350 A | 2/2000 | Price et al. | |
| 6,050,615 A | 4/2000 | Weinhold | |
| 6,079,678 A * | 6/2000 | Schott et al. | 248/229.15 |
| 6,105,212 A | 8/2000 | Wright | |
| 6,158,729 A | 12/2000 | Tsai | |
| 6,302,543 B1 * | 10/2001 | Arai et al. | 353/70 |
| 6,382,576 B1 | 5/2002 | Heimbrock | |
| 6,450,465 B1 * | 9/2002 | Eslick | 248/230.4 |
| 6,474,632 B1 | 11/2002 | Liou | |
| 6,523,799 B2 | 2/2003 | Su | |
| 6,585,243 B1 | 7/2003 | Li | |
| 6,793,186 B2 * | 9/2004 | Pedersen | 248/229.13 |
| 6,896,232 B2 | 5/2005 | Crowell et al. | |
| 6,957,795 B1 * | 10/2005 | Hsieh | 248/316.4 |
| 6,964,425 B2 | 11/2005 | Turner | |
| 7,073,755 B2 | 7/2006 | Michaud et al. | |
| 7,272,878 B2 | 9/2007 | Dixon | |
| 7,566,038 B2 | 7/2009 | Scott et al. | |
| 7,789,361 B2 * | 9/2010 | Bally et al. | 248/229.2 |
| 7,793,902 B2 * | 9/2010 | Buchanan et al. | 248/230.1 |
| 2006/0278785 A1 | 12/2006 | Wiesner et al. | |
| 2008/0077078 A1 | 3/2008 | Locke et al. | |

FOREIGN PATENT DOCUMENTS

| | | |
|---|---|---|
| WO | 2005067819 | 7/2005 |

OTHER PUBLICATIONS

Written Opinion for International Application No. PCT/EP2010/027610 dated Aug. 5, 2010, 6 pages.

International Preliminary Report on Patentability for Application No. PCT/US2010/027610 mailed Nov. 11, 2010, 9 pages.

* cited by examiner

RAPID ATTACH AND RELEASE CLAMPS

BACKGROUND

The present disclosure is in the general field of clamps for securing objects to supporting poles, and in particular, for supporting medical devices connected to a patient on a supporting structure or pole.

One of the more basic tools used in a medical environment is an intravenous ("IV") stand. The typical IV stand includes an elongated member, or pole, that may be oriented either vertically or horizontally, and may additionally have any one of a variety of cross-sectional geometric shapes, including round, hexagonal or square. The pole is placed upon and supported by a pedestal. Typically, IV devices such as supply bags or bottles of an IV liquid—normally blood, saline solution, or medication—are attached to the IV pole. These liquids are then delivered via a thin tube to a patient who is in a bed adjacent the IV stand.

As medical technologies and treatment techniques have advanced, the number of different IV liquids that are delivered to a patient has increased. As such, there are often additional devices that must be attached to the IV stand to manage, control, measure, and monitor the delivery of these various liquids. One such device is an infusion pump. In some situations, there may be more than one infusion pump, and there may be a controller or microcontroller that controls the infusion pumps. These devices are designed to attach to an IV stand, such as an IV pole, and allow for the attachment of numerous other devices in a collective and orderly fashion.

To minimize equipment costs and increase flexibility of use, these devices are typically required to be adaptable for use with various types of IV stands and poles. To accomplish this, such devices have typically been mounted on an IV pole by way of a clamping assembly. However, there are several disadvantages inherent in the currently available clamping assemblies. These clamping assemblies are sometimes capable of attachment to the IV stand in only one position. Thus, they may not be used interchangeably between a horizontally disposed IV pole and a vertically disposed IV pole.

Some clamping assemblies are limited as to the size or shape, or both, of the IV pole to which they can attach. While a clamp on a clamping assembly may be capable of attaching to a round IV pole, it may not be capable of attaching to a hexagonal or square shaped pole. Some clamps are limited to specific widths or diameters of poles to which they can properly attach. Each of these limitations restricts the adaptability and limits the usefulness of the clamping assembly.

An additional drawback is the effort required for positioning the clamp on a pole or repositioning the clamp on the same pole or on a different pole. Some clamps require an extended amount of time and effort to manually attach the medical device to the pole. Quick timing may be important in administering a prescribed medication, and time spent to attach or disattach an infusion pump from a pole could be crucial. In any case, it is desirable to make the movement and attachment of medical equipment for use easier and less time consuming.

SUMMARY

The present disclosure provides rapid attached and release clamps that can be used to attach a medical device to a suitable support. For example, the clamps can be attached to IV poles, especially poles having a diameter ranging from about 9.5 mm (0.375 in) to about 38 mm (1.50 in), although different embodiments may be used on poles of other diameters. While most IV poles are cylindrical, with a circular cross-section, the clamp may also be used on supports or poles with other outside shapes such as rectangular, square, or elliptical shapes.

In an embodiment, the present disclosure provides a clamp. The clamp includes a threaded rod and a knob constructed and arranged to interlock with the threaded rod. The knob has an exterior surface and an interior surface and defines a passageway. A lock having a threaded portion is rotatably attached to the interior surface of the knob. The lock is constructed and arranged to move between a closed position with the threaded portion engaged with a threaded rod positioned in the passageway and an open position with the threaded portion not engaged with the threaded rod. A lever is moveably attached to the knob and constructed and arranged to rotate the lock about a pivot point.

The passageway of the knob can have a circular diameter. The exterior surface of the knob can comprise a gripping handle and a circular base. The gripping handle can have an S-shape. In addition, the exterior surface of the knob can define one or more gripping grooves.

In another embodiment, the present disclosure provides a clamp. The clamp includes a threaded rod and a knob constructed and arranged to interlock with the threaded rod. The knob has an exterior surface and an interior surface and defines a passageway. A platform defines a bore and is attached to the interior surface of the knob. A stud is slideably attached to the platform within the bore. A lock having a threaded portion is rotatably attached to the interior surface of the knob. The lock is also attached to one side of the stud. A lever is moveably attached to the knob and constructed and arranged to move the lock by applying force to an opposing side of the stud. The lock is constructed and arranged to move between a closed position with the threaded portion entering the passageway and an open position with the threaded portion not entering the passageway.

The knob can further include one or more springs positioned between the lock and the platform. The spring is constructed and arranged to press the threaded portion of the lock into the passageway.

In an alternative embodiment, the present disclosure provides a rapid attach and release clamp that includes a knob having an exterior surface and an interior surface. The knob defines a passageway extending from a top portion of the knob to a bottom portion of the knob. A platform defines a bore and is attached to the interior surface of the knob. A stud is slideably attached to the platform within the bore. A lock having a threaded portion is rotatably attached to the interior surface of the knob. The lock is also attached to one side of the stud. A lever is moveably attached within a side aperture of the knob and constructed and arranged to move the lock by applying force to an opposing side of the stud. The lock is constructed and arranged to move between a closed position with the threaded portion entering the passageway and an open position with the threaded portion not entering the passageway.

The clamp can further include a rod that is constructed and arranged to be inserted into the passageway of the knob. The rod comprises a threaded portion that releasably interlocks with the threaded portion of the lock.

An arm comprises a first limb pivotably attached to a second limb that is attached to the rod. A portion of at least one of the first limb and the second limb can be made of a frictional material. The first limb can be angled towards the threaded portion of the rod, and the second limb can be angled away from the threaded portion of the rod. The second limb can further have an extension for attaching to a medical device. The arm can also have a biasing mechanism that causes the first limb to be pivoted away from the second limb in the absence of any force applied to the first limb.

In yet another embodiment, the present disclosure provides a method of securing a medical device to a support. The method includes providing a clamp according to alternative embodiments of the present disclosure. The medical device is attached to an arm of the clamp. The clamp is attached to the support so that the support is positioned between a first limb and a second limb of the arm and a rod from the clamp. The lever can be pressed so a lock from a knob of the clamp is in the open position and the knob is moved down the rod so that the knob is contacting a first limb of the arm. The lever can be released and the knob then rotated to tighten the clamp around the support. The support can be a pole that is part of an IV stand.

It is accordingly an advantage of the present disclosure to provide an improved clamp for attaching medical devices to a structure.

It is another advantage of the present disclosure to provide a rapid attach clamp for quickly attaching a medical device to a pole.

It is yet another advantage of the present disclosure to provide a rapid release clamp for quickly releasing a medical device from a pole.

Additional features and advantages are described herein, and will be apparent from the following Detailed Description and the figures.

DETAILED DESCRIPTION

Figure 1:
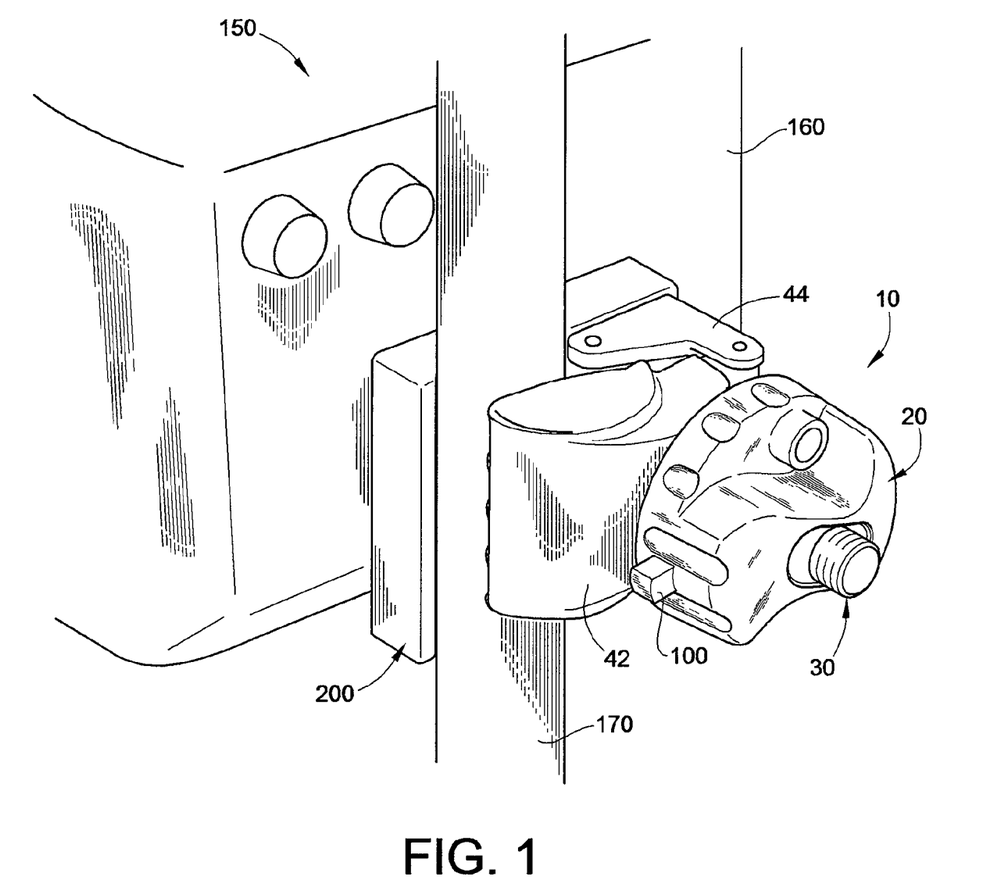
FIG. 1 is a perspective view of one embodiment of a rapid attach and release clamp of the present disclosure, which is shown securing a medical device to a pole.

Referring now to the drawings and in particular to FIG. 1, one embodiment of the rapid attach and release clamp 10 of the present disclosure operating with a medical device system 150 is illustrated. Clamp 10 and the various components of clamp 10 can be made using any suitable materials such as metals, polymers and plastics. Thus, clamp 10 can be designed to have a light weight, high strength, and durability. System 150 includes clamp 10, support base 200, a medical device 160, such as a infusion pump, and an intravenous ("IV") support pole 170. Any suitable medical device 160 can be used in system 150.

Clamp 10 enables medical device 160 to be easily clamped and unclamped to support pole 170, allowing device 160 to be moved up and down as necessary. Clamp 10 also allows medical device 160 to be rotated about pole 170 and clamped at a desired radial position relative to support pole 170.

Figure 2:
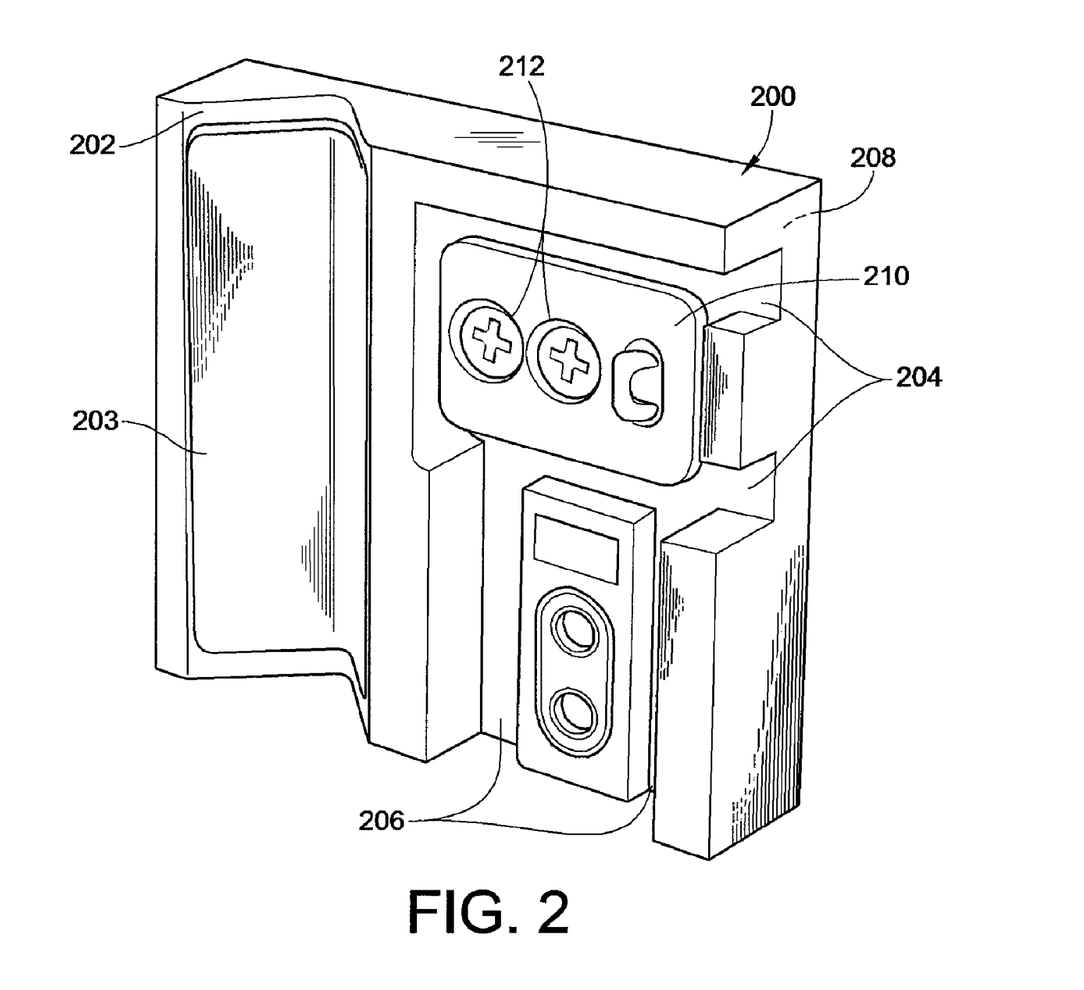
FIG. 2 is a perspective view of one embodiment of a support base of the present disclosure.

As illustrated in FIG. 2, in an embodiment, support base 200 contains a section defining a channel 202 that is shaped to be positioned on one side of support pole 170. Support base 200 also contains a section having a first pair of slots 204 and a second pair of slots 206 that are configured to be attached to clamp 10. Support base 200 further contains a locking plate 210 attached to support base 200 between the first pair of slots 204. Alternatively, locking plate 210 can be attached to support base 200 between the second pair of slots 206. Locking plate 210 is removably attached to support base 200 via a suitable method such as one or more screws 212 as illustrated.

The backside 208 of support base 200 opposite channel 202 and locking plate 210 is removably or permanently attached to medical device 160, as seen in FIG. 1, using any suitable attachment method. For example, support base 200 can be attached to medical device 160 (or other devices) by one or more screws or fasteners. Alternatively, support base 200 can be attached to medical device 160 (or other devices) using adhesives or welding techniques.

Figure 3:
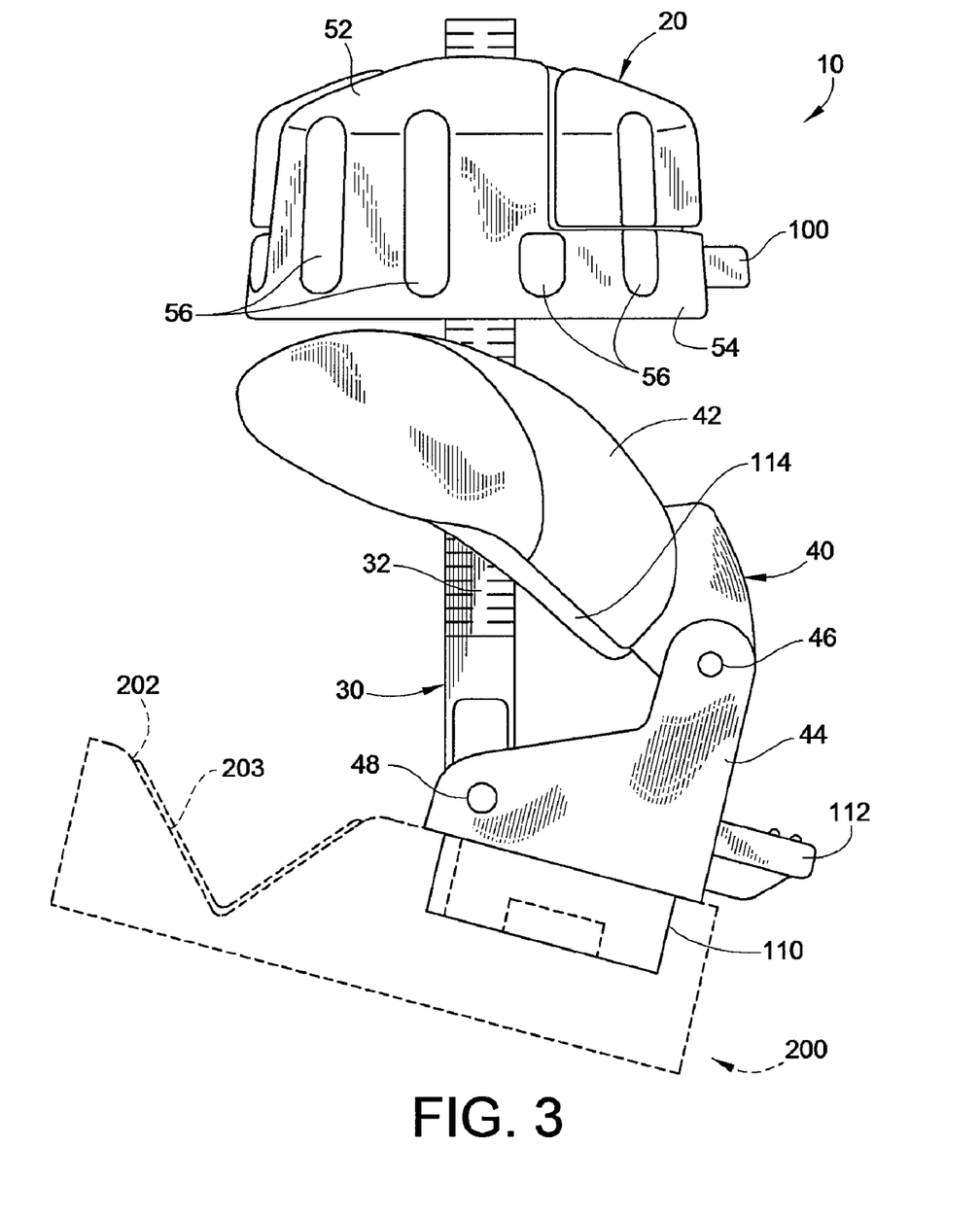
FIG. 3 is side elevation view of one embodiment of a rapid attach and release clamp of the present disclosure.
Figure 4:
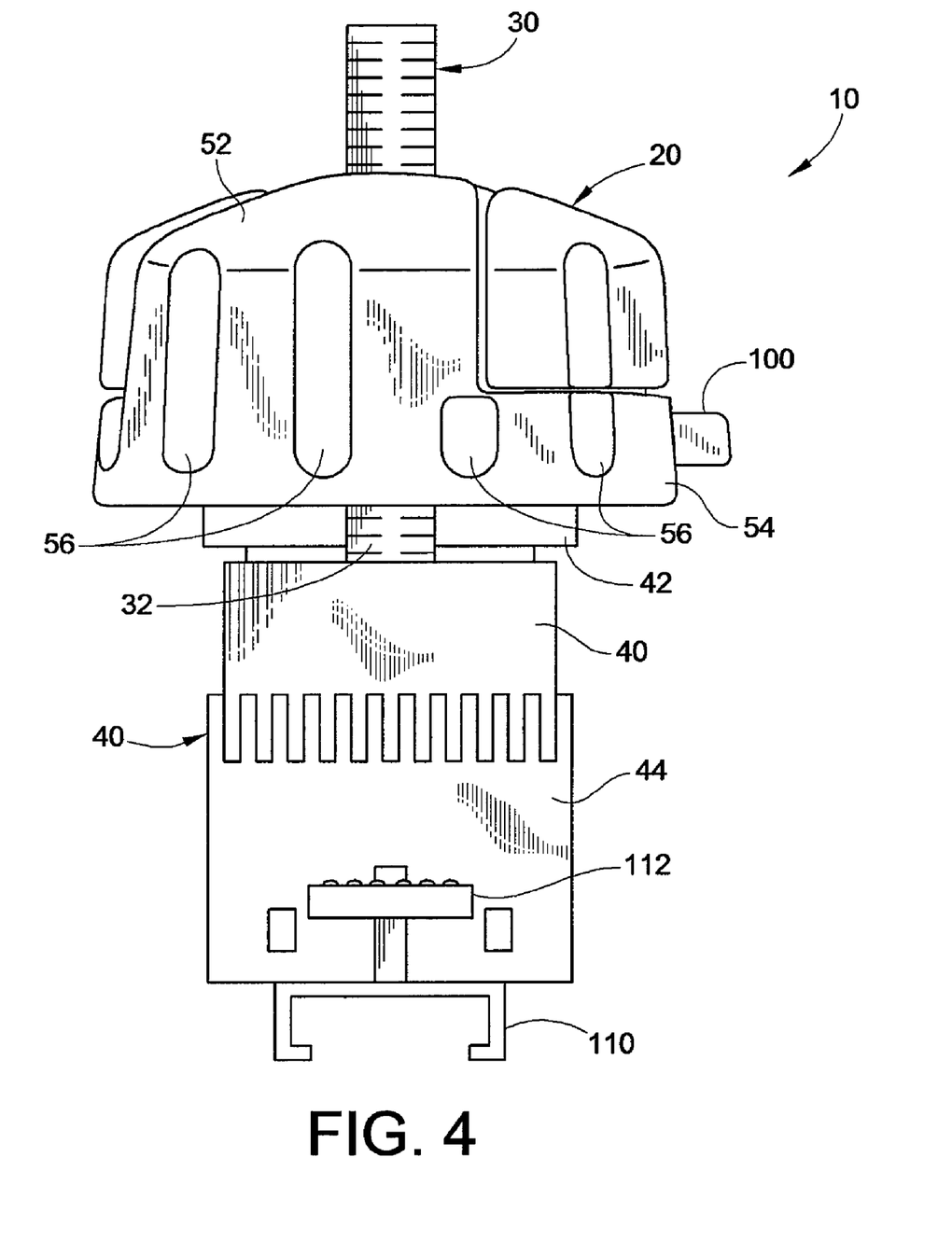
FIG. 4 is rear elevation view of one embodiment of a rapid attach and release clamp of the present disclosure with the knob pressing down on the arm.
Figure 5:
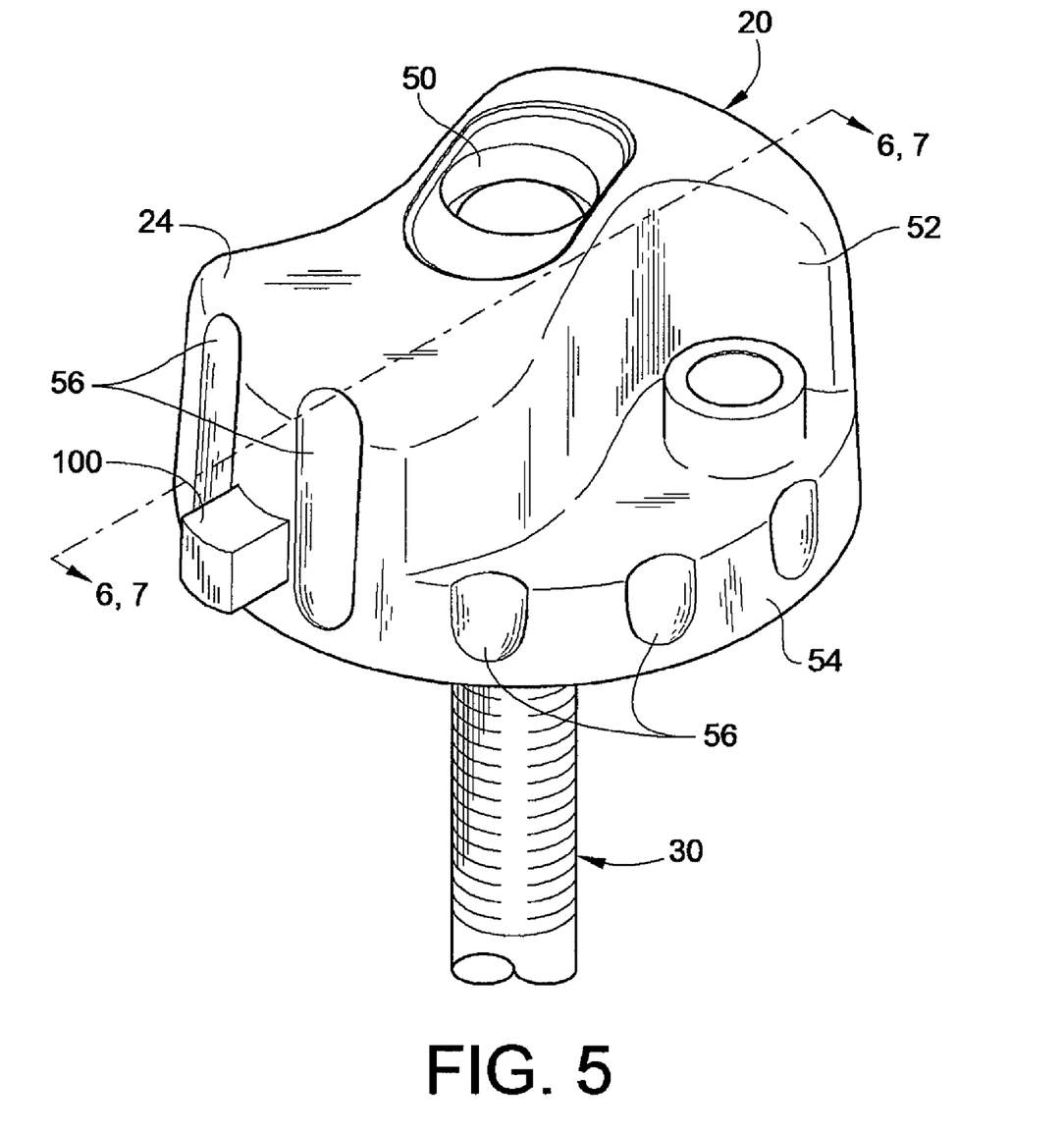
FIG. 5 is front perspective view of one embodiment of a knob and rod of the present disclosure.
Figure 6:
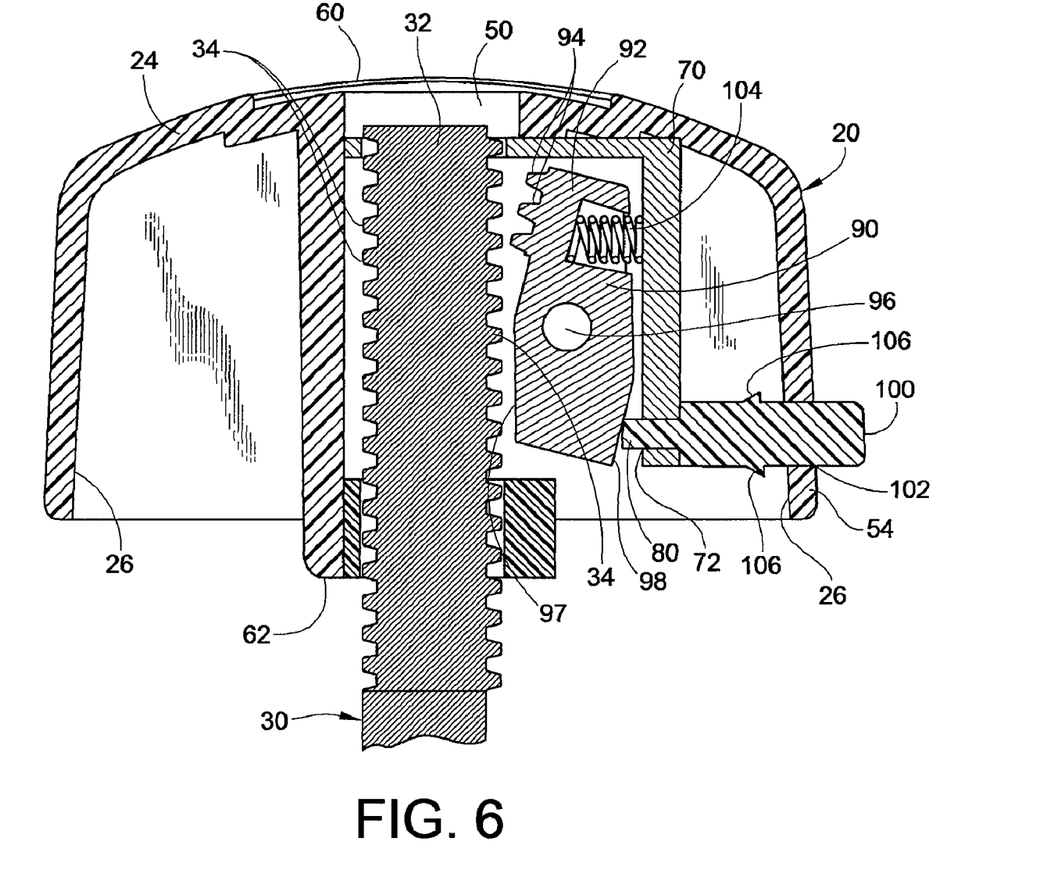
FIG. 6 is a cross-section view taken along line VI-VI of the knob and rod shown in FIG. 5 in a locked position.
Figure 7:
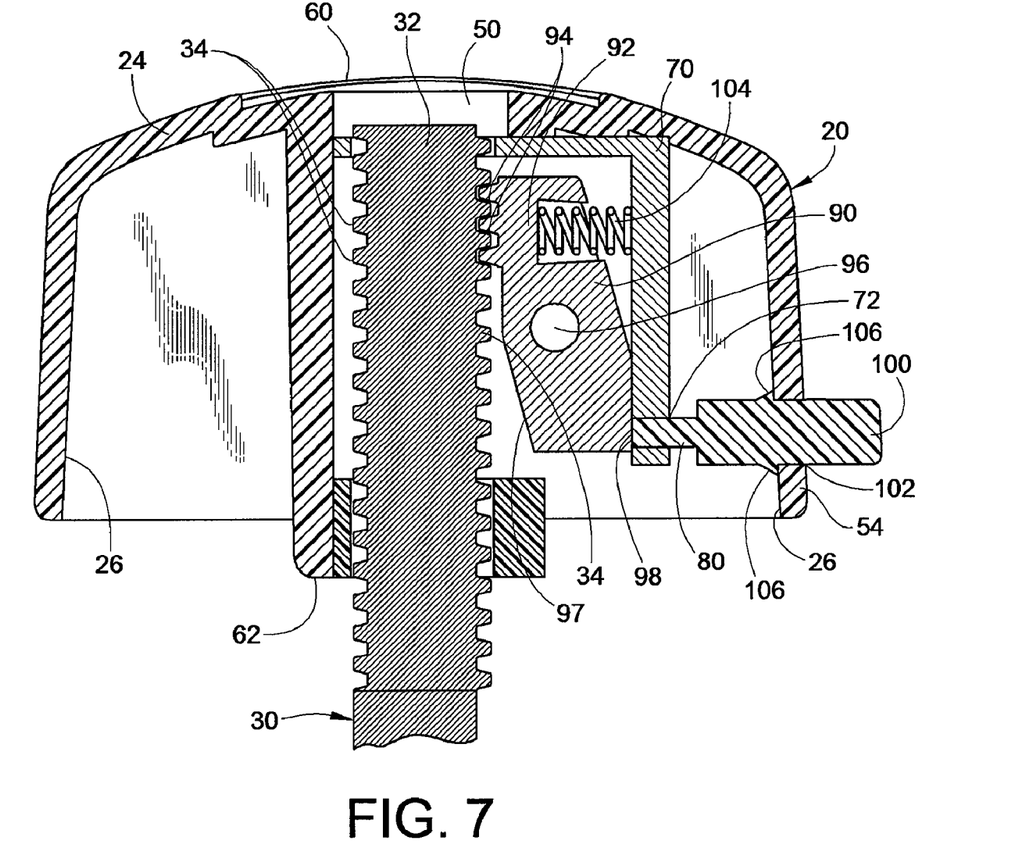
FIG. 7 is a cross-section view taken along line VII-VII of the knob and rod shown in FIG. 5 in a released position.

As illustrated in FIGS. 3 to 7, in an embodiment, clamp 10 includes a knob 20, a rod 30 and an arm 40 that is attached to rod 30. Rod 30 is constructed and arranged to be inserted into a passageway 50 (FIG. 5) of knob 20. Rod 30 includes a threaded portion 32 having a plurality of male threads 34 that releasably interlock with the one or more female threads 94 of threaded portion 92 of lock 90 (FIGS. 6 and 7). The threaded portion 34 can extend through the top of knob 20 as knob 20 is rotated clockwise, causing an inward (downward as seen in FIG. 3) translational advancement of knob 20 along threaded portion 34. The diameter of rod 30 can range from about 0.6 cm (0.25 inches) to about 1.3 cm (0.5 inches). The length of rod 30 can range from about 3.8 cm (1.5 inches) to about 12.7 cm (5 inches).

As further illustrated in FIG. 3, in an embodiment, arm 40 includes a first limb 42 pivotably attached to a second limb 44 via a pivot point 46. Second limb 44 is in turn pivotally attached to rod 30 via pivot point 48. Pivot point 46 allows first limb 42 to be angled towards threaded portion 32 of rod 30. Pivot point 48 allows second limb 44 to be angled away from threaded portion 32 of the rod 30. The length of first limb 42 and second limb 44 can range from about 3.8 cm (1.5 inches) to about 7.6 cm (3 inches).

Clamp 10 can be attached to support base 200 to tightly secure medical device 160 to support pole 170. In the illustrated embodiment of FIGS. 3 and 4, second limb 44 contains a release mechanism 112 that allows slotted attachment 110 to be reasonably locked in place with locking plate 210 of support base 200. Release mechanism 112 may be spring loaded to provide a quick-disconnect type connection. Release mechanism 112 can also be activated by pressing release mechanism 112 towards base plate 200 to unsecure and easily slide slotted attachment 110 out of the first pair of slots 204. In an alternative embodiment, clamp 10 can also include a biasing mechanism (not shown) that causes first limb 42 to be pivoted towards or away from second limb 44 in the absence of any force applied to first limb 42 with knob 20.

In the illustrated embodiment, first limb 42 includes a high friction coefficient material pad 114 such as rubber. First limb 42 can itself be alternatively be made from a high friction coefficient material. Likewise, channel 202 can be provided with a high friction coefficient material. The high friction coefficient material acts to prevent clamp 10 from undesirably moving or sliding along support or IV pole 170 to which clamp 10 is attached.

As illustrated in detail in FIGS. 5 to 7, knob 20 has an exterior surface 24 and an interior surface 26. Knob 20 defines passageway 50 that extends from a top portion 60 of the knob 20 to a bottom portion 62 of knob 20. The outer peripheral border of passageway 50 of knob 20 has a circular diameter in the illustrated embodiment. In an embodiment, the inner diameter of passageway 50 ranges from about 0.6 cm (0.25 inches) to about 1.4 cm (0.55 inches). In alternative embodiments, passageway 50 can have a different cross-sectional shape as long as it is large enough to receive rod 30.

The shape of knob 20 enables a user to be able to readily grasp and rotate knob 20. For example, exterior surface 24 of knob 20 can have a gripping handle 52 and a circular base 54. In an embodiment, knob 20 has a height ranging from about 2.5 cm (1 inch) to about 7.6 cm (3 inches), and circular base 54 has a diameter/width ranging from about 2.5 cm (1 inch) to about 7.6 cm (3 inches). In alternative embodiments, base 54 can have rectangular, square, polygonal or elliptical shapes.

Gripping handle 52 has an S-shape in the illustrated embodiment so as to receive the user's thumb and forefinger. In addition, exterior surface 24 of knob 20 can define one or more gripping grooves 56. Gripping handle 52 and gripping grooves 56 allow a user to easily grasp and twist knob 20 during the operation of clamp 10.

FIGS. 6 and 7 show that knob 20 houses a platform 70. Platform 70 defines a bore 72 and is attached to interior surface 26 of knob 20. Platform 70 is alternatively molded with knob 20. Bore 72 of platform 70 secures a stud 80 that is slideably received within the bore. Stud 80 is constructed and arranged to move back and forth within platform 70 when a user applies a designated amount of pressure to a lever 100 attached to or formed integrally with stud 80.

A lock 90, having a threaded or toothed portion 92 having one or more threads or teeth 94, is rotatably attached to interior surface 26 of knob 20 via hinge point 96. Lock 90 can be metal or plastic and is rigid enough to be placed under stress when interlocked with threads 34 of threaded portion 32 as seen in FIG. 7. Because lock 90 is constructed and arranged to rotate about a pivot point 96 as seen in FIGS. 6 and 7, a surface 97 is chamfered to allow lock 90 to be in the open position of FIG. 6. Lock 90 is attached to or abutted against the stud 80. Lock 90 has a second chamfered surface 98 that allows lock 90 to be rotated to the position of FIG. 7, so that surface 98 remains abutted against stud 80 for a subsequent activation.

Lever 100 is slideably attached within an aperture 102 of knob 20 and is shaped at its outside end to be pressed by a user. Lever 100 is confined between lock 90 and tabs 106 formed on lever 100, which abut inner surface 26 when lock 90 is engaged with rod 30.

Lever 100 is constructed and arranged to move lock 90 via stud 80 when a force is applied to lever 100. For example, when lever 100 is pushed inward, lever 100 forces stud 80 inward, which forces lock 90 to rotate about pivot point 96. In this manner, lock 90 moves between a locked or closed position (see FIG. 7) with threads or teeth 94 from threaded portion 92 engaging threads 34 of rod 30 and an open position (see FIG. 6) with threads or teeth 94 from threaded portion 92 disengaging from threads 94.

Knob 20 can include a biasing mechanism 104, for example a spring, which is positioned between lock 90 and platform 70. Spring 104 is constructed and arranged to press threads or teeth 94 of threaded portion 92 of lock 90 into engagement with threads 34 or teeth of rod 30 when lever 100 is not pressed. As used herein, the term "biasing mechanism" includes mechanical springs and other compressible biasing elements, such as, compressible rubber or other elastomeric dome elements and solid compressible elastomeric bodies.

Although the figures illustrate that teeth 94 of lock 90 are attached to a side of rod 30, in alternative embodiments, threads 94 of lock 90 can extend around differently sized portions of rod 30, e.g., ¼ or halfway around rod 30.

Clamp 10 is used in conjunction with support base 200 to tightly secure medical device 160 to support pole 170, so that a user can readily move medical device 160 up and down. As illustrated in FIGS. 3 and 4, second limb 44 includes a slotted attachment 110. Slotted attachment 110 of clamp 10 is configured to slide into first pair of slots 204 or second pair of slots 206 of support base 200 (see FIG. 2) and be locked into place on support base 200. With support base 200 attached to medical device 160 as illustrated in FIG. 1, one side of support pole 170 fits within groove 202. The opposite side of support pole 170 is contacted by first limb 42 of arm 40, which presses support pole 170 against support base 200.

As seen in FIGS. 6 and 7, in one clamping operation, when lock 90 is in the locked position shown in FIG. 7, the user can tighten clamp 10 about IV pole 170 by rotating knob 20 towards arm 40 (e.g., clockwise, depending on the design of threaded portion 32). Knob 20 can be rotated clockwise and translates, via its threaded engagement with rod 30, along rod 30 towards arm 40. As knob 20 is rotated towards arm 40, teeth or threads 94 of lock 90 wind around threads 34 of rod 30 causing the translational movement.

Knob 20 contacts first limb 42 and compresses first limb 42 towards the angled edge of second limb 44. At this time, support pole 170 is squeezed between support base 200 and first limb 42 of arm 40 as seen in FIG. 1. In particular, first limb 42 squeezes support pole 170 into groove 202 of support base 200. In this manner, support pole 170 is tightly secured between support base 200 and arm 40 of clamp 10. Support base 200 and arm 40 can be constructed and arranged to accommodate any suitably sized and shaped diameter IV pole 170.

If desired, the user may rapidly move knob 20 by pressing lever 100, causing lock 90 to be in the open position shown in FIG. 6. The user can then extend or translate knob 20 freely (for course adjustment of knob 20 relative to pole 170) along rod 30 without the need to rotate knob 20. This action prevents the user from spending unnecessary time and energy rotating knob 20 to initially engage contact arm 40 or pulling knob 20 away from arm 40.

When knob 20 has reached a desired position or contacts first limb 42 of arm 40, lever 100 is depressed, allowing lock 90 to assume the locked position of FIG. 7. If knob 20 is only lightly engaging or compressing arm 40 onto support pole 170, the user can further lock clamp 10 onto support pole 170 enough to firmly hold the weight of medical device 160, by turning knob 20 in the clockwise direction (for fine adjustment of knob 20 relative to pole 170).

To release clamp 10, the user can unscrew knob 20, for example by turning knob 20 counterclockwise, thereby releasing the holding compression on arm 40. Next, the user can push lever 100 to quickly disengage threads 94 of lock 90 from threads 34 of rod 30. Accordingly, the user can readily lift knob 20 off of rod 30, so that the grip of arm 40 around pole 170 is quickly loosened for adjustment of the medical device. The medical device along with clamp 10 can then be rapidly removed from the support.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical device clamp comprising:
   a threaded rod;

an arm pivotally attached to the threaded rod; and
a knob including:
- (i) an exterior surface and an interior surface defining a passageway, the threaded rod extending through the passageway;
- (ii) a lock including a threaded or toothed portion, the lock rotatably attached to the interior surface of the knob, the lock constructed and arranged to move between a closed position with the threaded or toothed portion engaging the threaded rod and an open position with the threaded or toothed portion not engaging the threaded rod; and
- (iii) a lever moveably attached to the knob and constructed and arranged to rotate the lock from the closed position to the open position.

2. The medical device clamp of claim 1 further comprising at least one spring constructed and arranged to press the lock into the closed position.

3. The medical device clamp of claim 1, wherein the exterior surface of the knob includes at least one of a gripping handle and a circular base, the gripping handle having an S-shape for gripping and turning the knob.

4. A medical device pole clamp comprising:
a threaded rod;
an arm attached to the rod; and
a knob including:
- (i) an exterior surface and an interior surface defining a passageway, the threaded rod extendable through the passageway;
- (ii) a lock having a threaded or toothed portion, the lock being rotatably attached via a pivot to the interior surface of the knob, the lock in communication with one side of a lever, and
- (iii) a lever spring-loaded to move the threaded or toothed portion into engagement with the threaded rod, the lever constructed and arranged to rotate the threaded or toothed portion about the pivot and away from the rod via a manual force applied to the lever.

5. The medical device pole clamp of claim 4, wherein the exterior surface of the knob includes at least one of a gripping handle and a circular base, the gripping handle having an S-shape for grasping and turning the knob.

6. The medical device pole clamp of claim 4, wherein the arm is attached to a base plate, the arm and the base plate configured to clamp about a pole to support a medical device.

7. The medical device pole clamp of claim 6, the base plate configured to be coupled to the medical device.

8. The medical device pole clamp of claim 6, wherein the base plate includes a channel shaped to clamp to the pole to support the medical device.

9. The medical device pole clamp of claim 6, the arm including a first limb attached pivotally to a second limb, the second limb attached to the base plate, the first limb moved by the knob to clamp the pole between the first limb and the base plate.

10. The medical device pole clamp of claim 6, wherein at least one of the arm and the base plate includes high coefficient of friction material to engage the pole frictionally.

11. A medical device pole clamp comprising:
a threaded rod;
an arm attached to the rod; and
a knob including:
- (i) an exterior surface and an interior surface defining a passageway, the threaded rod extendable through the passageway;
- (ii) a lock having a threaded or toothed portion, the lock being rotatably attached via a pivot to the interior surface of the knob, the lock in communication with one side of a lever,
- (iii) a lever spring-loaded to move the threaded or toothed portion into engagement with the threaded rod, the lever constructed and arranged to rotate the threaded or toothed portion about the pivot and away from the rod via a manual force applied to the lever; and
- (iv) a platform defining a bore, the lever moveable slideably within the bore.

12. The medical device pole clamp of claim 11, the lever including a stud portion that moves slideably within the bore.

13. A medical device pole clamp comprising:
a threaded rod;
an arm attached to the rod; and
a knob including:
- (i) an exterior surface and an interior surface defining a passageway, the threaded rod extendable through the passageway;
- (ii) a lock having a threaded or toothed portion, the lock being rotatably attached via a pivot to the interior surface of the knob, the lock in communication with one side of a lever, wherein the lock defines a beveled edge to aid the threaded or toothed portion in being rotated away from the rod, and
- (iii) a lever spring-loaded to move the threaded or toothed portion into engagement with the threaded rod, the lever constructed and arranged to rotate the threaded or toothed portion about the pivot and away from the rod via a manual force applied to the lever.

* * * * *